(12) United States Patent
Wang et al.

(10) Patent No.: US 7,429,613 B2
(45) Date of Patent: Sep. 30, 2008

(54) PROCESS FOR THE PREPARATION OF ATORVASTATIN AND INTERMEDIATES

(75) Inventors: Fan Wang, Hamilton (CA); Daqing Che, Brantford (CA); Bhaskar Reddy Guntoori, Brantford (CA); Yajun Zhao, Brantford (CA); Aaron C. Kinsman, London (CA); Jody Faught, Brantford (CA); Alan Chow, Kitchener (CA)

(73) Assignee: Apotex Pharmachem Inc., Brantford, Ontario (CA)

( * ) Notice: Subject to any disclaimer, the term of this patent is extended or adjusted under 35 U.S.C. 154(b) by 0 days.

(21) Appl. No.: 11/487,500

(22) Filed: Jul. 17, 2006

(65) Prior Publication Data

US 2006/0252816 A1    Nov. 9, 2006

Related U.S. Application Data

(62) Division of application No. 11/099,624, filed on Apr. 6, 2005, now Pat. No. 7,112,604.

(30) Foreign Application Priority Data

Feb. 28, 2005    (CA) .................................. 2498978

(51) Int. Cl.
*A61K 31/4025* (2006.01)
*C07D 207/327* (2006.01)
(52) U.S. Cl. ...................... 514/423; 548/537
(58) Field of Classification Search ............... 514/423; 548/537
See application file for complete search history.

(56) References Cited

U.S. PATENT DOCUMENTS

| | | | |
|---|---|---|---|
| 4,681,893 A | 7/1987 | Roth | 514/422 |
| 5,003,080 A | 3/1991 | Butler et al. | 548/517 |
| 5,273,995 A * | 12/1993 | Roth | 514/422 |
| 5,298,627 A | 3/1994 | Butler et al. | 548/517 |

OTHER PUBLICATIONS

Roth, B.D., et al., "Inhibitors of Cholesterol Biosynthesis. 3. Tetrahydro-4-hydroxy-6-[2-(1H-pyrrol-1-yl)ethyl]-2H-pyran-2-one Inhibitors of HMG-CoA Reductase. 2. Effects of Introducing Substituents at Positions Three and Four of the Pyrrole Nucleus", *J. Med. Chem.*, (1991), 34, 357-366.

* cited by examiner

*Primary Examiner*—Rei-tsang Shiao
*Assistant Examiner*—Joseph R Kosack
(74) *Attorney, Agent, or Firm*—Marcelo K. Sarkis; Ivor M. Hughes; Neil H. Hughes

(57) ABSTRACT

A process is provided for preparing (R)-5-[2-(4-fluorophenyl)-5-(1-methylethyl)-3-phenyl-4-[(phenylamino)carbonyl]-1H-pyrrol-1-yl]-5-hydroxy-3-oxo-1-heptanoic acid, R-substituted ester 9 comprising:

(a) reacting the aldehyde 1 with the enolate form of (S)-2-hydroxy-1,2,2-triphenylethyl acetate substituent in a chelating co-solvent;

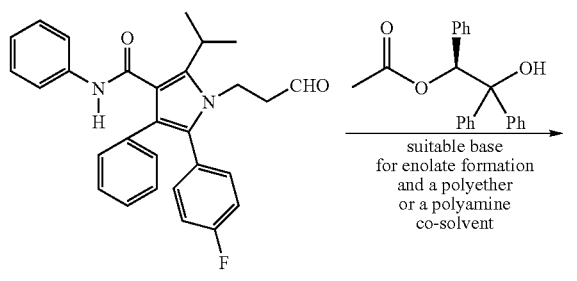

(b) hydrolysis of (R,S)-5-[2-(4-fluorophenyl)-5-(1-methylethyl)-3-phenyl-4-[(phenylamino)carbonyl]-1H-pyrrol-1-yl]-3-hydroxy-1-pentanoic acid, (S)-2-hydroxy-1,2,2-triphenylethyl ester (2a and 2b) using a base, preferably an alkali metal base, preferably in a solvent to form the carboxylic acid 7;

(c) treating the acid 7 with a chiral base to form a salt and purifying the salt to obtain enantiomerically enriched (R)-7 chiral base salt;

(d) alkylation of the (R)-7 chiral base salt or the free base derived from (R)-7, forming (R)-5-[2-(4-fluorophenyl)-5-(1-methylethyl)-3-phenyl-4-[(phenylamino)carbonyl]-1H-pyrrol-1-yl]-5-hydroxy-3-oxo-1-heptanoic acid, R-substituted ester 9 and atorvastatin calcium 6,

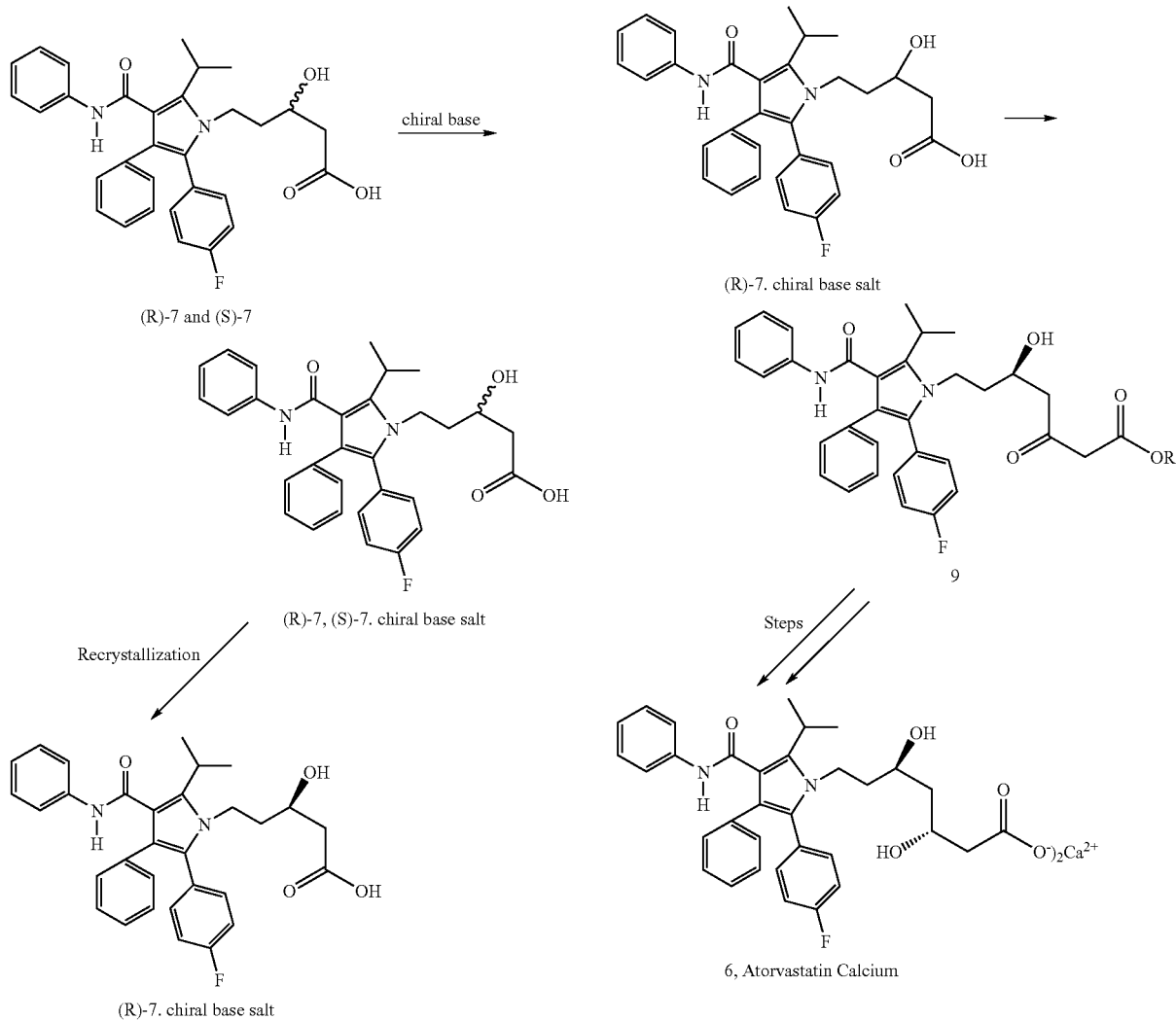

wherein R is a C1 to C6 alkyl, C6 to C9 aryl or C7 to C10 aralkyl.

7 Claims, 4 Drawing Sheets

PROCESS FOR THE PREPARATION OF ATORVASTATIN AND INTERMEDIATES

This application is a divisional of application Ser. No. 11/099,624, filed Apr. 6, 2005 now U.S. Pat. No. 7,112,604.

FIELD OF THE INVENTION

The present invention relates to processes for preparing intermediates useful in the manufacture of Atorvastatin and pharmaceutically acceptable salts thereof and to the intermediates themselves useful in preparing Atorvastatin and pharmaceutically acceptable salts thereof.

BACKGROUND OF THE INVENTION

Atorvastatin is a reductase inhibitor of the enzyme 3-hydroxy-3-methylglutarate-coenzyme A (HMG-CoA) and therefore is a useful anti-hyperlipoproteinemic agent. It has proven to be a highly effective medication for the treatment of disorders such as hyperlipidemia and hypercholesterolemia which are conditions that are known risk factors for arteriosclerosis and coronary heart disease. Atorvastatin is chemically [R—(R*,R*)]-2-(4-fluorophenyl)-β,δ-dihydroxy-5-(1-methylethyl)-3-phenyl-4-(phenylcarbamoyl)-1H-pyrrole-1-heptanoic acid and is marketed as its calcium salt under the brand name Lipitor™.

A route to make Atorvastatin 6 is disclosed in U.S. Pat. No. 5,273,995. Depicted in Scheme 1 herein is a sequence of reactions from the process taught in U.S. Pat. No. 5,273,995 which involves the alkylation of aldehyde 1 to form ester 2 followed by transesterification to methylester 3 using sodium methoxide. Methylester 3 is then reacted with the lithium enolate of tert-butylacetate to form the β-ketoester 5, which is then further reacted over a series of steps to form Atorvastatin Calcium 6. If scale-up of the transformation 1 to 5 were contemplated, it would suffer from serious deficiencies. These include:

(a) The aldol reaction has low stereoselectivity (R,S:S,S 84:16) for this case and further recrystallisation steps would be necessary to obtain diastereopure material with a low overall yield (less than 40%).

(b) Silica gel column purification would be necessary to purify the β-hydroxy methylester 3.

(c) The disclosure is silent regarding the recovery of the expensive chiral auxiliary [(S)-1,1,2-triphenyl-1,2-ethanediol, 4].

(d) The initial transesterification step employs the expensive, flammable and corrosive base sodium methoxide and anhydrous conditions.

(e) Sodium methoxide is also a strong base which is expected to lead to detrimental side reactions.

(f) Further, example 3 of the patent requires the addition of the β-hydroxy methylester 3 in absolute THF to the lithium enolate solution "as quickly as possible without allowing the temperature to rise above −40° C.".

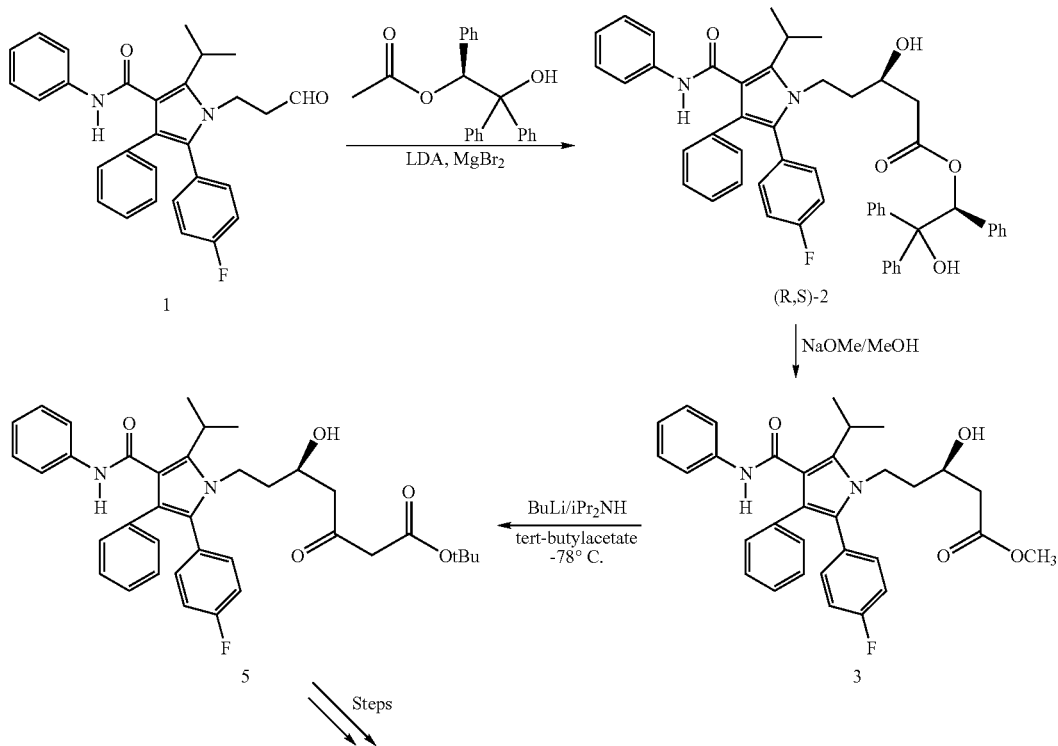

Scheme 1

-continued

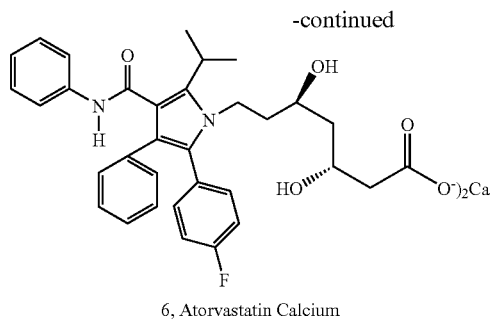

6, Atorvastatin Calcium

Recently disclosed in Canadian Patent application 2,460,935 is an improved preparation of hydroxy acid 7 from the aldol product 2 as depicted in Scheme 2. This process requires the establishment of the correct stereochemistry prior to hydrolysis step.

fication to provide enantiomerically enriched compound in the following step would be more facile. Thus according to such aspect, the following process set out in Scheme 3 is provided whereby a more stereoselective aldol reaction was unexpectedly obtained by the addition of a chelating co-

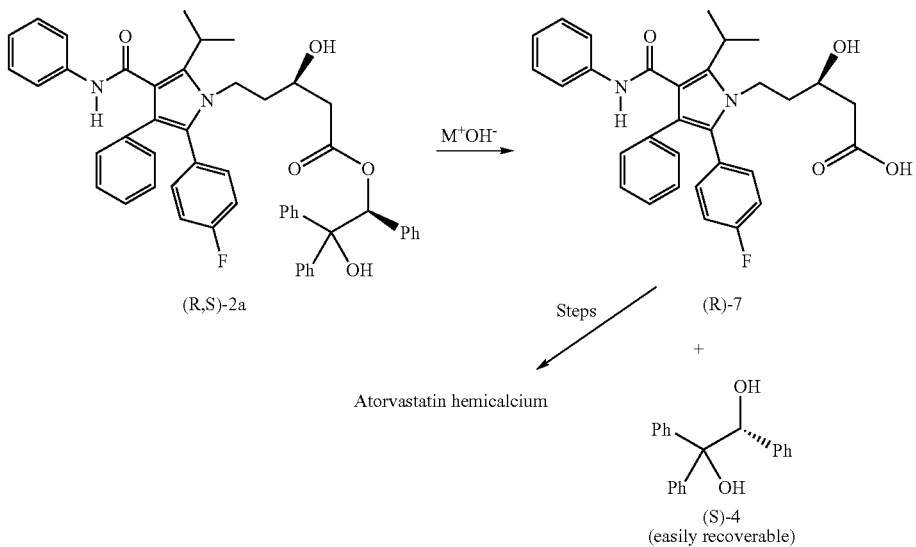

It is therefore an object of this invention to provide processes which overcome deficiencies of the prior art. It is a further object of this invention to provide a facile and commercially viable process to produce atorvastatin calcium 6 in enantiomerically enriched form.

Further and other object of this invention will be realized by those skilled in the art from the following Summary of the Invention and the Examples thereof.

SUMMARY OF THE INVENTION

According to one aspect of the invention there is provided a process to make intermediates useful to make Atorvastatin which involves improved stereoselectivity of the aldol reaction. This improvement is of importance since only the R,S diastereomer 2a (Scheme 3) can be used for the next steps, and the S,S-diastereomer 2b is regarded as by-product. If the stereoselectivity is improved, the yield of the desired R,S-diastereomer would be higher and more importantly, the purisolvent such as a polyether or a polyamine. This led to a higher ratio of the desired diastereomer (R,S)-2a relative to (S,S)-2b.

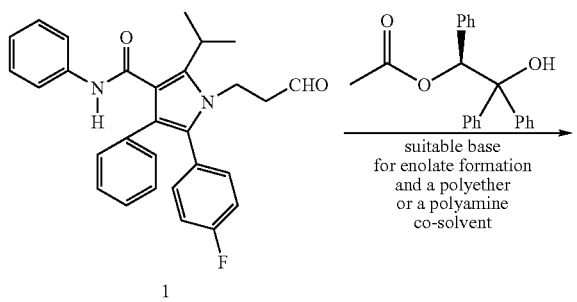

-continued

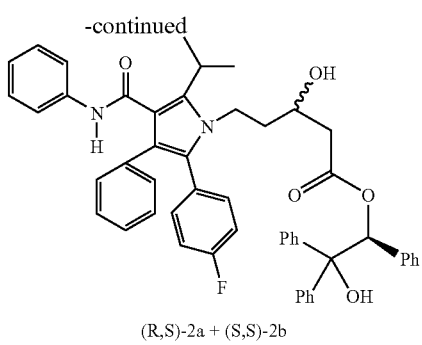

(R,S)-2a + (S,S)-2b

Furthermore, surprisingly and unexpectedly we have found that when 7, which is obtained for (R,S)-2a and (S,S)-2b (Scheme 4), is treated with a chiral organic base such as (R)-methylbenzylamine in an organic solvent or mixture of organic solvents, the diastereomeric acid 7/chiral base salt mixture is easily resolved or enantiomerically enriched. Examples of suitable organic solvents include C1 to C6 alkanols or a C4 to C8 cyclic or acyclic ethers or mixtures thereof. It is important to recognize that the chiral amine base can be recovered at a later step in the process and thereby recycled.

Scheme 4

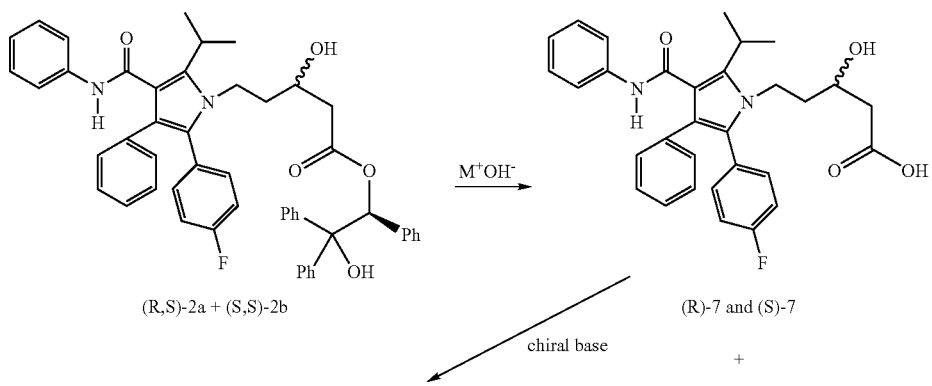

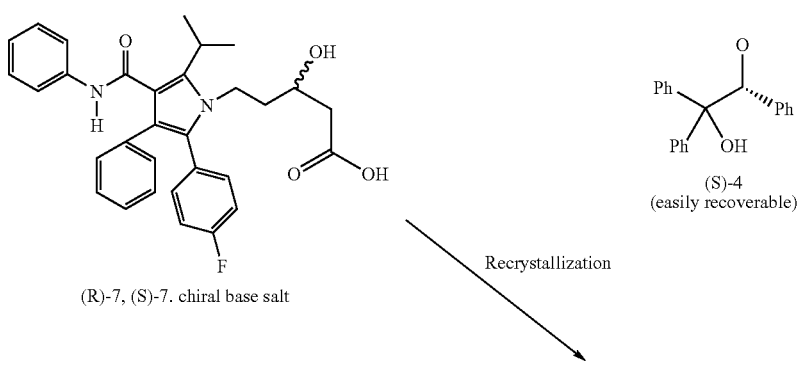

(R)-7, (S)-7. chiral base salt (S)-4
(easily recoverable)

Recrystallization

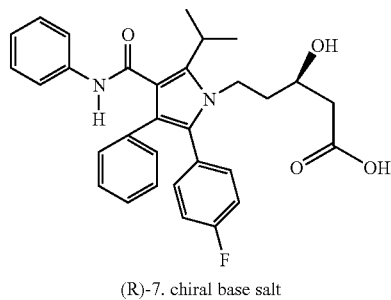

(R)-7. chiral base salt

According to yet another aspect of the invention, we have discovered a novel and more soluble crystalline form of the starting aldehyde 1, which we have designated as Form II, when using the process depicted in Scheme 5. This aldehyde is distinguished from the one previously described Roth et al. (J. Med. Chem. 1991, 34, 357-366), which we refer to herein as Form I. It is advantageous to have a more soluble aldehyde since it improves the next step (as depicted in Scheme 3) in terms of reaction volumes and production efficiency.

-continued

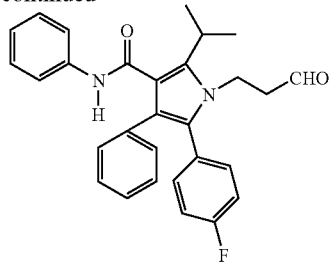

1

According to another aspect of this invention, the resolved hydroxy acid 7 can be used directly for β-keto ester 9 as depicted in Scheme 6, or if desired, be converted to its methyl ester 3 (Scheme 1) through conventional methods. The hydroxy acid 7 prepared from aldol product 2 in enantiomerically enriched form or in its racemic form (1:1 when no chiral auxiliary is used in the aldol reaction), can be resolved into its enantiomerically enriched form when treated with a chiral organic base in an organic solvent or solvents mixture. The formed diastereomeric salt can be easily purified through recrystallization to reach a diastereomeric excess of greater than about 99%. The enantiomerically enriched free hydroxy acid (R)-7 can then be recovered by treatment with acid or used directly in the next step.

Thus, an overall process for manufacturing Atorvastatin involving the various aspects of these inventions is depicted in Scheme 6 below.

Scheme 5

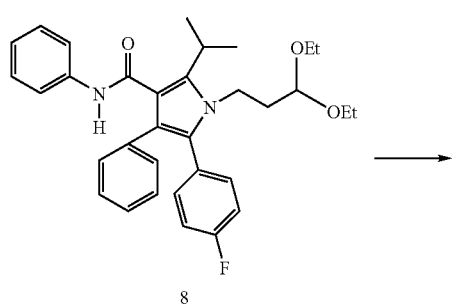

8

Scheme 6

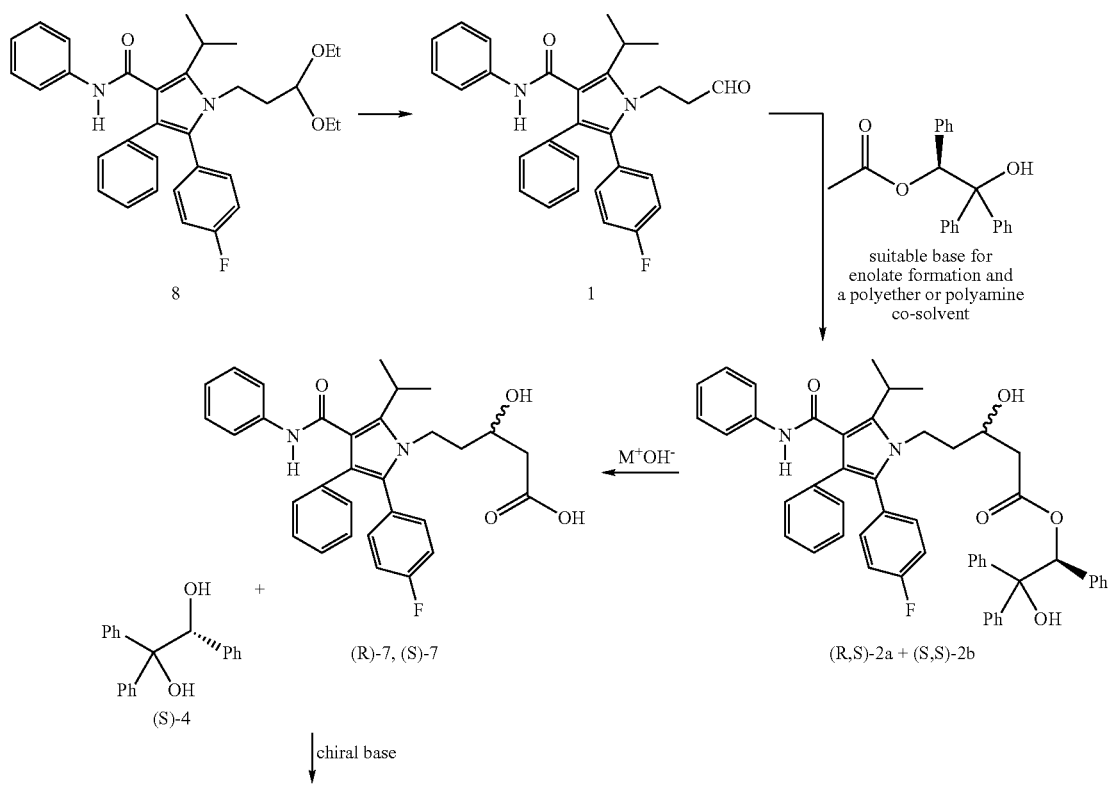

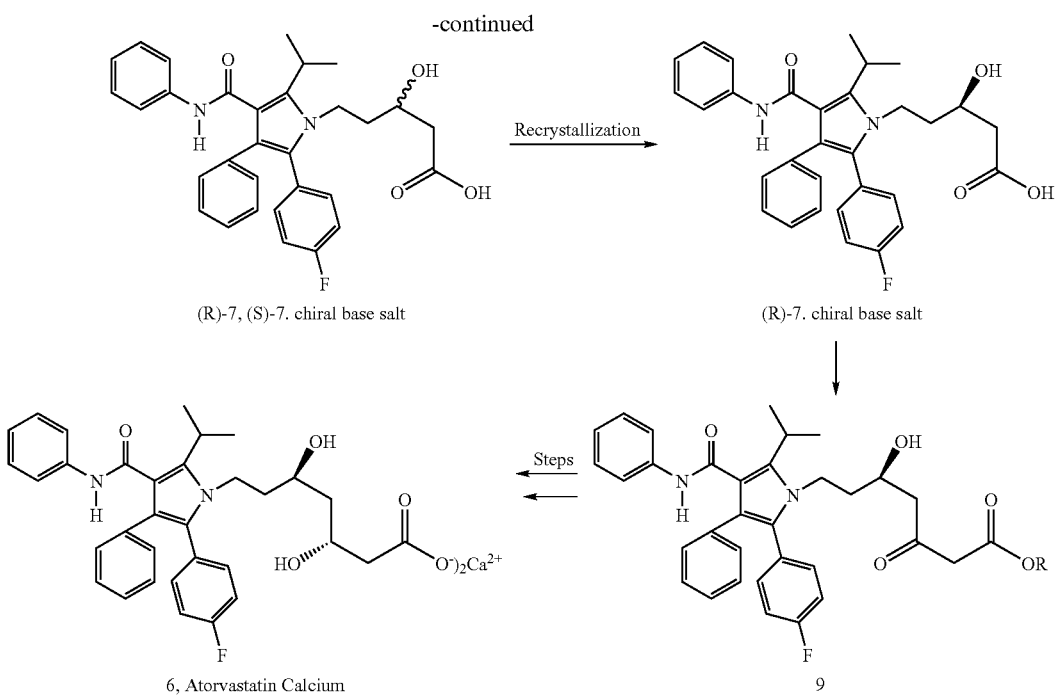

It has been unexpectedly and surprisingly discovered that the selectivity of aldol reaction depicted in Scheme 3 is improved to R,S:S,S 95:5 ratio when a chelating co-solvent such as polyether or polyamine is used. Furthermore, it has also been found that the presence of the magnesium ion as described in the original process is not required thereby simplifying the process.

Examples of chelating co-solvents that are suitable for the aldol reaction include polyamines and polyethers. Examples of polyamines include N,N,N',N'-tetramethylethylenediamine and examples of polyethers include dimethoxy ether, diethoxy ether or dioxane. Particularly suitable co-solvents are dimethoxy ether or diethoxy ether. A preferred suitable co-solvent is dimethoxy ether.

There are numerous advantages of this route compared to the original process of the U.S. Pat. No. 5,273,995. The use of a chelating co-solvent not only eliminates the laborious magnesium bromide preparation and addition, it also surprisingly improves the stereoselectivity from 84:16 to 95:5 (2a:2b) which in turn simplifies the subsequent purification step to furnish the optically enriched compound. Thus, the overall yield may be improved and the waste by-products are accordingly decreased.

According to another aspect of the invention, a process used in the manufacture of Atorvastatin and intermediates suitable for use to make Atorvastatin is provided wherein the intermediate material is easily purified and in enantiomerically enriched form. Thus, it has been also found that the aldol product can be hydrolyzed and the resulting carboxylic acid formed may then be reacted with a chiral base, for example a chiral amine such as (R)-methylbenzylamine to form a crystalline salt [(S)- and (R)-7], which surprisingly, can be easily recrystallized to give an optically enriched salt [(R)-7, Scheme 4]. Of note is that (R)-7 has the correct stereochemistry for further conversion to Atorvastatin. The hydrolysis reaction may be carried out using an alkali metal hydroxide, such as the preferred hydroxide, lithium hydroxide.

This hydrolysis reaction forms the β-hydroxy carboxylic acid 7 intermediate that is easily isolable and stable. When the enantiomerically enriched (R)-7 chiral base salt is isolated by this process, it may be used without purification for further elaboration to 9 and eventually Atorvastatin 6 and its calcium salt, or other salts. The conversion of 9 to 6 may be done based on procedures known in the art. The β-hydroxy carboxylic acid 7 prepared by the processes of this invention also has good handling properties and is easily dried.

An advantageous feature is that the hydrolysis reaction to form the β-hydroxy carboxylic acid 7 can be accomplished in a solvent that is also suitable for the salt formation step.

The salt formation involves a chiral base, which has the advantage of forming a diastereomeric mixture if the carboxylic acid is not already in enantiomerically enriched form. The advantage thereof is that the salt can be recrystallized and the optically enriched form can be generated and isolated.

Examples of the chiral bases can be commercially available natural occurring alkaloids or amines, or commercially available synthetic chiral amines. Particularly suitable examples can be commercially available chiral amines. More particularly suitable example can be (R)- or (S)-methylbenzylamine.

According to another aspect of this invention is that, if desired, the optically enriched β-hydroxy carboxylic acid (R)-7 intermediate prepared by the processes of this invention can be converted to the methylester 3 using standard esterification methods known in the art.

According to another aspect of this invention, if desired, one can directly convert 2 into 9 without isolation of the intermediate β-hydroxy carboxylic acid 7. This variation has further advantages including cost-effectiveness. For instance, the conversion of 2 into 9 without isolation of 7 removes the necessity, of drying 7, thereby reducing the overall cycle time.

Further, once the aldol product is hydrolyzed, the resulting carboxylic acid can be easily enriched to higher optically purity by a simple salt formation with a suitable chiral base, for instance (R)-methylbenzylamine, in a suitable resolution solvent. The optically enriched carboxylic acid salt then can be used directly in the next step or in its free acid form after treatment with another acid such as aqueous HCl.

The above resolution is achieved by a process whereby the enantiomerically enriched or racemic hydroxy acid 7 is dissolved together with a chiral base such as (R)-methylbenzylamine and the like in a suitable organic solvent such as C1 to C6 alkanols or a C4 to C8 cyclic or acyclic ethers or mixtures thereof. Examples of suitable solvents for the resolution include methanol, ethanol, isopropanol and C4-C8 cyclic or acyclic ethers such as diethyl ether, dipropyl ether, dibutyl ether or methyl tert-butyl ether. The ratio of alcohol and ether can be about 1:5 to 5:1, preferably about 1:3 to 2:1, more preferably about 3:2. The mixture can be stirred at room temperature to reflux, preferably at reflux temperature for a long period of time, preferably about 5-20 hours, more preferably about 10-15 hours.

The desired (R)-enantiomer of the hydroxy acid 7 demonstrates a marked preference for forming a less soluble diastereomeric salt, which can be isolated by filtration.

The amount of chiral organic base can be 0.5 to 1.5 equivalents, preferably 0.8 to 1.2 equivalents.

According to another aspect of the invention, there is provided a process for preparing (R)-5-[2-(4-fluorophenyl)-5-(1-methylethyl)-3-phenyl-4-[(phenylamino)carbonyl]-1H-pyrrol-1-yl]-5-hydroxy-3-oxo-1-heptanoic acid, R-substituted ester 9, wherein R is a C1 to C6 alkyl, C6 to C9 aryl or C7 to C10 aralkyl comprising:
  (a) reacting the aldehyde 1 with acetate having a chiral alkoxy substituent in THF and a chelating co-solvent;
  (b) hydrolysis of (R)-5-[2-(4-fluorophenyl)-5-(1-methylethyl)-3-phenyl-4-[(phenylamino)carbonyl]-1H-pyrrol-1-yl]-3-hydroxy-1-pentanoic acid, (S)-2-hydroxy-1,2,2-triphenylethyl ester 2 using a base, preferably an alkali metal base, preferably selected from the group consisting of lithium hydroxide, sodium hydroxide or potassium hydroxide, preferably in a solvent to form the carboxylic acid 7;
  (c) treating the acid with a chiral base to form a salt and purifying the salt;
  (d) alkylation of the (R)-7 or the salt thereof forming (R)-5-[2-(4-fluorophenyl)-5-(1-methylethyl)-3-phenyl-4-[(phenylamino)carbonyl]-1H-pyrrol-1-yl]-5-hydroxy-3-oxo-1-heptanoic acid, R-substituted ester 9.

Preferably the solvent used during hydrolysis is methanol or water or a mixture thereof. The compound of formula 9 may then be converted to Atorvastatin, for example, Atorvastatin Calcium. The R substituent in 9 is a C1 to C6 alkyl, C6 to C9 aryl or C7 to C10 aralkyl. Preferably the R group is a tert-butyl group. For step (c) above, preferable bases are chiral amines, even more preferably (R)-methylbenzylamine.

According to yet another aspect of the invention, there is provided optically enriched (R)-5-[2-(4-fluorophenyl)-5-(1-methylethyl)-3-phenyl-4-[(phenylamino)carbonyl]-1H-pyrrol-1-yl]-3-hydroxy-1-pentanoic acid 7.

According to yet another aspect of the invention, there is provided salt of optically enriched (R)-5-[2-(4-fluorophenyl)-5-(1-methylethyl)-3-phenyl-4-[(phenylamino)carbonyl]-1H-pyrrol-1-yl]-3-hydroxy-1-pentanoic acid 7 and a chiral base.

According to yet another aspect of the invention, there is provided a process for the preparation of Atorvastatin or pharmaceutically acceptable salts thereof using the processes described herein.

According to yet another aspect of the invention, the intermediate (R)-5-[2-(4-fluorophenyl)-5-(1-methylethyl)-3-phenyl-4-[(phenylamino)carbonyl]-1H-pyrrol-1-yl]-3-hydroxy-1-pentanoic acid 7 is not isolated during the process.

According to yet another aspect of the invention, the salt of (R)-5-[2-(4-fluorophenyl)-5-(1-methylethyl)-3-phenyl-4-[(phenylamino)carbonyl]-1H-pyrrol-1-yl]-3-hydroxy-1-pentanoic acid 7 with a chiral base is isolated during the process.

According to yet another aspect of the invention of the invention, there is provided a process for the preparation of (R)-5-[2-(4-fluorophenyl)-5-(1-methylethyl)-3-phenyl-4-[(phenylamino)carbonyl]-1H-pyrrol-1-yl]-3-hydroxy-1-pentanoic acid, methylester 3 from (R)-5-[2-(4-fluorophenyl)-5-(1-methylethyl)-3-phenyl-4-[(phenylamino)carbonyl]-1H-pyrrol-1-yl]-3-hydroxy-1-pentanoic acid 7 or its salt form of a chiral base which comprises:
  (a) hydrolysis of (R)-5-[2-(4-fluorophenyl)-5-(1-methylethyl)-3-phenyl-4-[(phenylamino)carbonyl]-1H-pyrrol-1-yl]-3-hydroxy-1-pentanoic acid, (S)-2-hydroxy-1,2,2-triphenylethyl ester 2 using a base, preferably an alkali metal base, preferably selected from the group consisting of lithium hydroxide, sodium hydroxide or potassium hydroxide, preferably in a solvent to form the acid 7;
  (b) treating the acid with a chiral base to form a salt and purifying the salt.

According to yet another aspect of the invention, there is provided a process for the preparation of (R)-5-[2-(4-fluorophenyl)-5-(1-methylethyl)-3-phenyl-4-[(phenylamino)carbonyl]-1H-pyrrol-1-yl]-3-hydroxy-1-pentanoic acid 7 comprising hydrolysis of (R)-5-[2-(4-fluorophenyl)-5-(1-methylethyl)-3-phenyl-4-[(phenylamino)carbonyl]-1H-pyrrol-1-yl]-3-hydroxy-1-pentanoic acid, (S)-2-hydroxy-1,2,2-triphenylethyl ester 2, wherein the said hydrolysis is carried out using a base.

According to another aspect of the invention, the process the use of a novel more soluble crystalline form, which we have designated as Form II, of the starting aldehyde 1. This novel and more soluble crystalline form of the starting aldehyde 1 was obtained when 8 is treated in aqueous HCl and acetone, as depicted in Scheme 5, to produce a new crystalline form, designated as Form II, of the aldehyde 1 which has a melting point of 164-165° C. Compared to Form I, Form II is more soluble in organic solvents such as tetrahydrofuran, dimethoxyethane, and dioxane, and this has the advantage that a smaller amount of solvent can be used which reduces the production cost.

For comparative purposes, the DSC thermogram of the prior art Form I polymorph is shown in FIG. 1 and a PXRD diffractogram as shown in FIG. 2. The newly discovered Form II polymorph has a DSC thermogram as shown in FIG. 3 and a PXRD diffractogram as shown in FIG. 4.

BRIEF DESCRIPTION OF THE FIGURES

Reference will be had to the following figures wherein.

Figure 1:
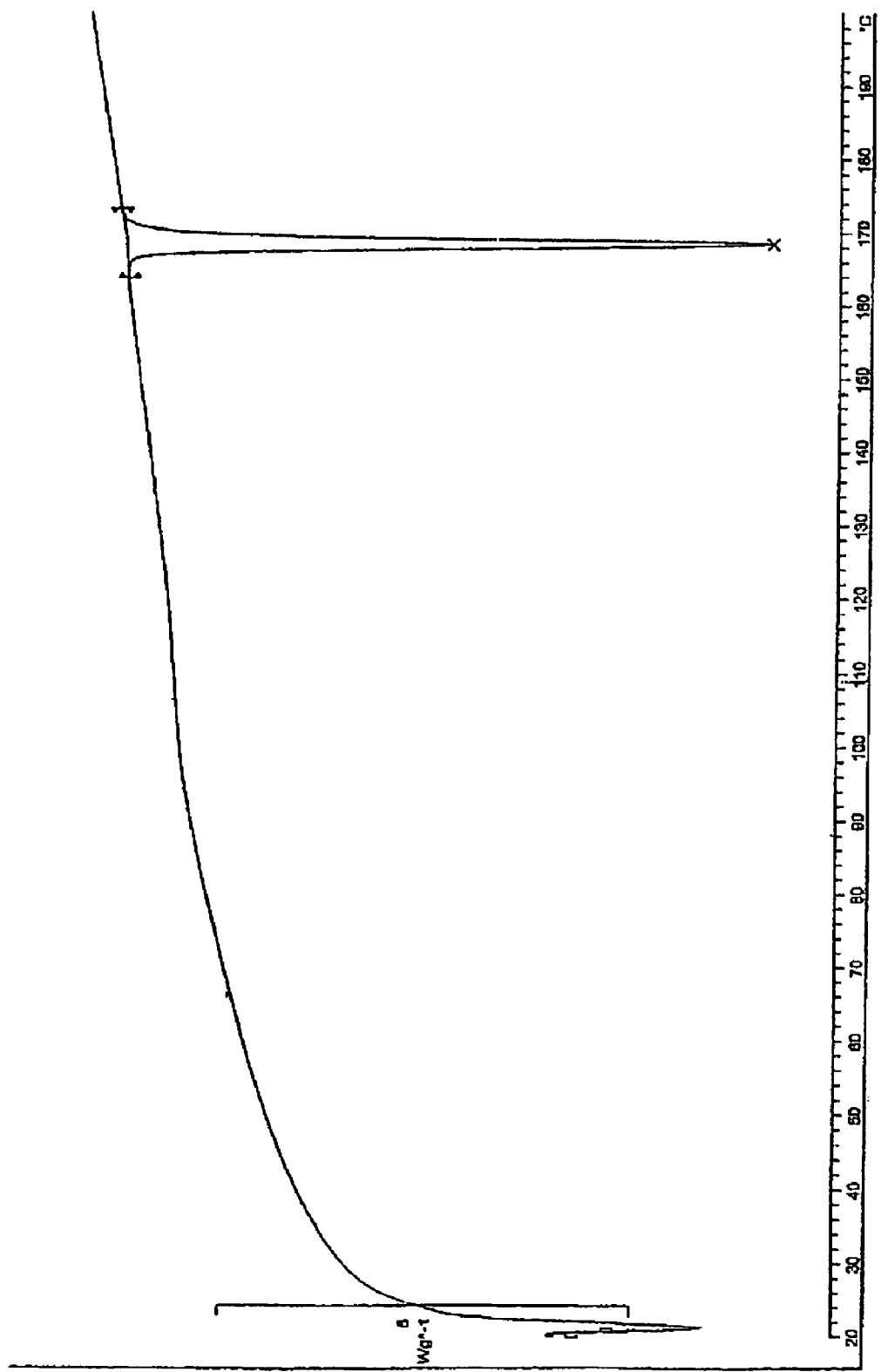
FIG. 1 is the DSC thermogram of the prior art Form I polymorph.
Figure 2:
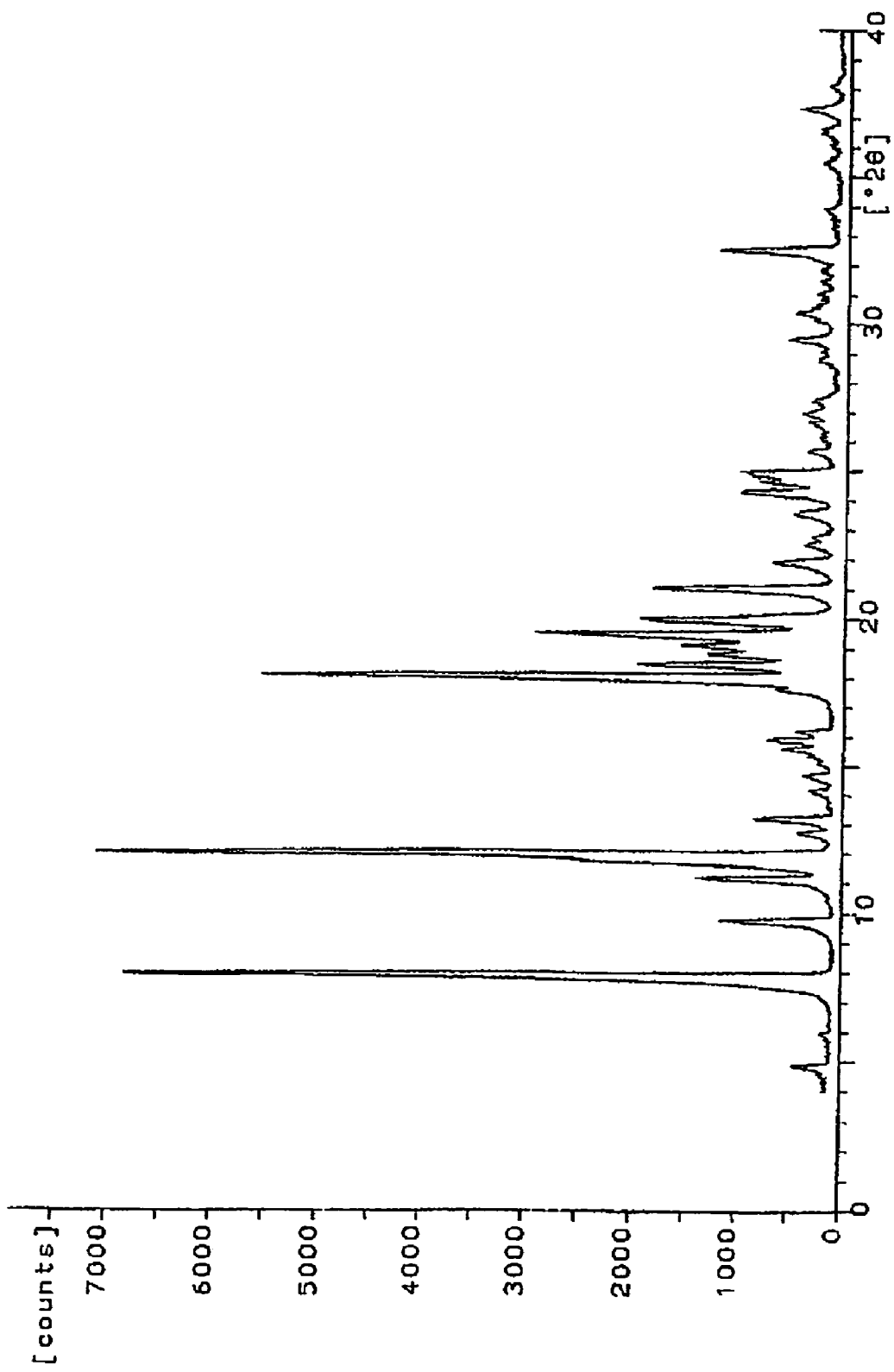
FIG. 2 is PXRD diffractogram.

The following examples exemplify various aspects of the invention.

EXAMPLES

Example 1

Preparation of (R)-5-[2-(4-fluorophenyl)-5-(1-methylethyl)-3-phenyl-4-[(phenylamino)carbonyl]-1H-pyrrol-1-yl]-3-hydroxy-1-pentanoic acid, (S)-2-hydroxy-1,2,2-triphenylethyl ester 2

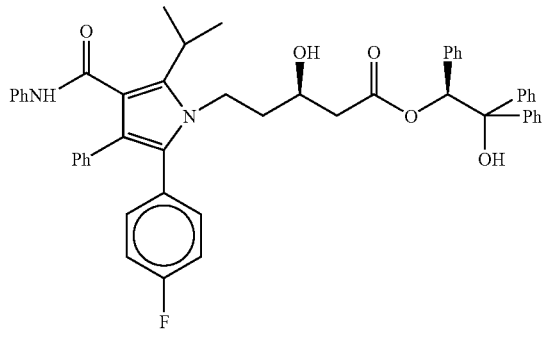

To a suspension of S-(−)-2-Hydroxy-1,2,2-triphenylethyl acetate (40.2 g) in 300 mL anhydrous THF at −10 to 0° C. was added a solution of LDA prepared by reaction of diisopropylamine (46.5 mL) with 2.5 M n-BuLi/hexanes (97 mL) in 300 mL anhydrous THF at −5 to 0° C. After stirring at 0° C. for 30 min the mixture was cooled to −78° C. Then, a solution of 5-(4-fluorophenyl)-2-(1-methylethyl)-1-(3-oxopropyl)-N,4-diphenyl-1H-pyrrole-3-carboxamide 1 (50 g) in 280 mL anhydrous THF was added dropwise and maintained at −78° C. for 30 min. After adding 25 mL AcOH and 250 mL water the mixture was allowed to warm to room temperature. The layers were separated and the organic layer was washed and dried. After evaporation of the solvent the crude product was obtained (94 g). Analytical data are consistent with that from the prior art.

HPLC: 86:14 R:S-form

Example 2

Preparation of 5-[2-(4-fluorophenyl)-5-(1-methylethyl)-3-phenyl-4-[(phenylamino)carbonyl]-1H-pyrrol-1-yl]-3-hydroxy-1-pentanoic acid methylbenzylamine salt

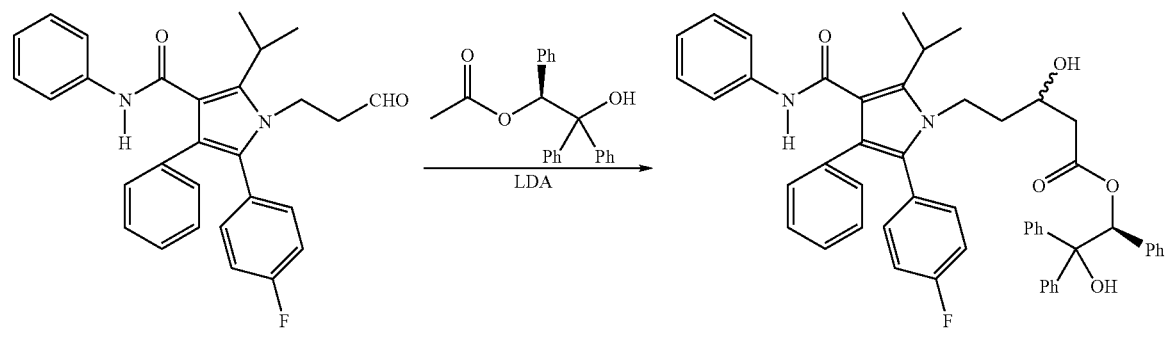

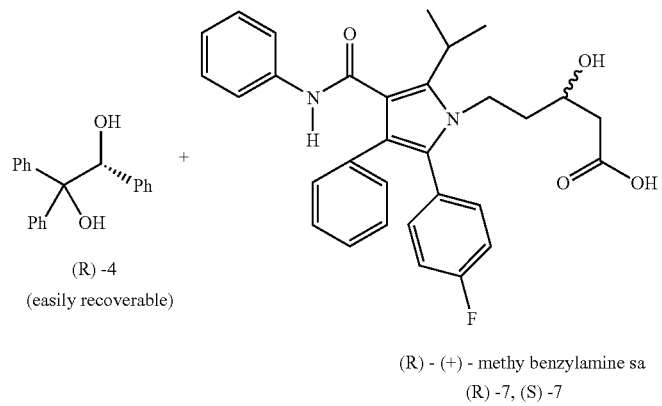

To a suspension of S-(−)-2-Hydroxy-1,2,2-triphenylethyl acetate (40.2 g) in 250 mL anhydrous 1,2-dimethoxyethane at −10 to 0° C. was added a solution of LDA prepared by reaction of diisopropylamine (46.5 mL) with 2.5 M n-BuLi/hexanes (97 mL) in 300 mL anhydrous THF at −5 to 0° C. After stirring at 0° C. for 30 min the mixture was cooled to −78° C. Then, a solution of 5-(4-fluorophenyl)-2-(1-methylethyl)-1-(3-oxopropyl)-N,4-diphenyl-1H-pyrrole-3-carboxamide (50 g) in 250 mL anhydrous 1,2-dimethoxyethane was added dropwise and maintained at −78° C. for 30 min. At this point a sample was taken and treated as EXAMPLE 1 and HPLC showed 2a:2b 95:5. After adding 100 mL MeOH, followed by 100 mL water the mixture was allowed to warm to room temperature then refluxed for 3 hours. After adding 700 mL water the mixture was evaporated to remove the organic solvents. To the mixture was added 450 mL methanol and heated to reflux for 30 min. After cooling to room temperature the recovered crude (S)-1,1,2-triphenylethanediol 4 was collected by filtration and washed with 500 mL of MeOH/water (1:1). The solid was dried to give 32 g 4 (90% recovery). The filtrate was evaporated to remove methanol followed by adding 250 mL ethyl acetate. The mixture was acidified with aq. HCl and the layers were separated. The aqueous layer was extracted with ethyl acetate. The combined organic layers were washed with brine and evaporated to dryness. (R)-(+)-methylbenzylamine (16 g), 230 mL methanol and 460 mL methyl t-butyl ether were added and the mixture was heated to reflux and maintained for 6 hours. After cooling to room temperature the product 7-methylbenzylamine salt was filtered and dried (52 g). The analytical data are consistent with the assigned structure.

Chiral HPLC: 97.8:2.2 (R,S/S,S)

$^1$H-NMR (400 MHz, DMSO-d6): δ/ppm=1.34-1.40(m, 9H), 1.50-1.62(m, 2H), 1.98-2.07 (m, 2H), 3.18-3.29(m, 1H), 3.60-3.66(m, 1H), 3.73-3.81(m, 1H), 3.91-3.98(m, 1H), 4.13-4.18(m, 1H), 6.50-6.88(br, 3H), 6.95-7.13(m, 6H), 7.16-7.28 (m, 7H), 7.32-7.36(t, 2H, J=15.2), 7.40-7.46(d, 2H, J=7.3 Hz), 7.50-7.52(d, 2H, J=8.0 Hz), 9.8(s, 1H).

Example 3

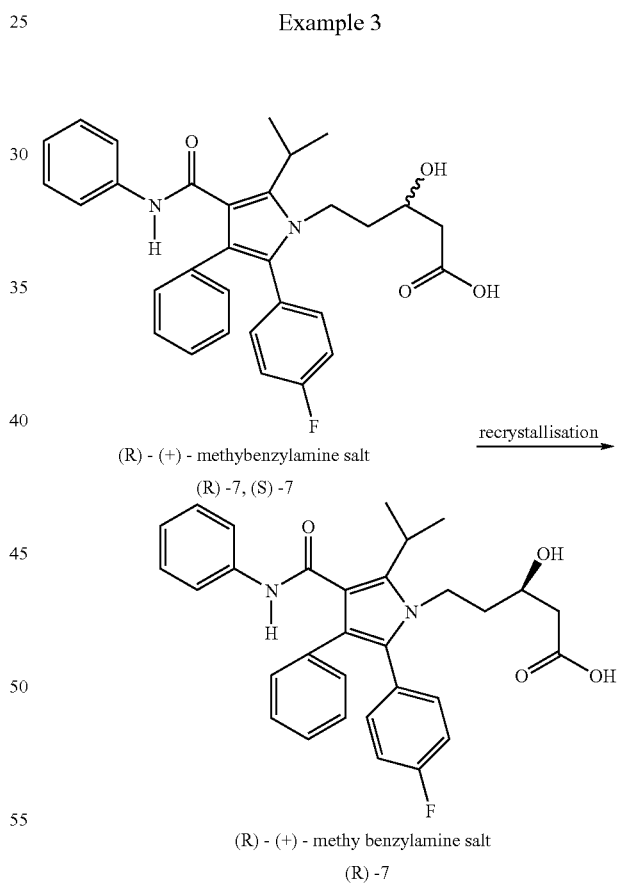

A suspension of 7-methylbenzylamine salt (52 g, R,S:S,S, 97.8:2.2) in 200 mL MTBE and 150 mL MeOH was heated to reflux and maintained for 14 hours. After cooling to room temperature the product (R)-7-methylbenzylamine salt was isolated by filtering, washing with MeOH/MTBE (2:1) and drying (46 g). The analytical data are consistent with the assigned structure.

Chiral HPLC: >99:1 (R,S/S,S)

Example 4

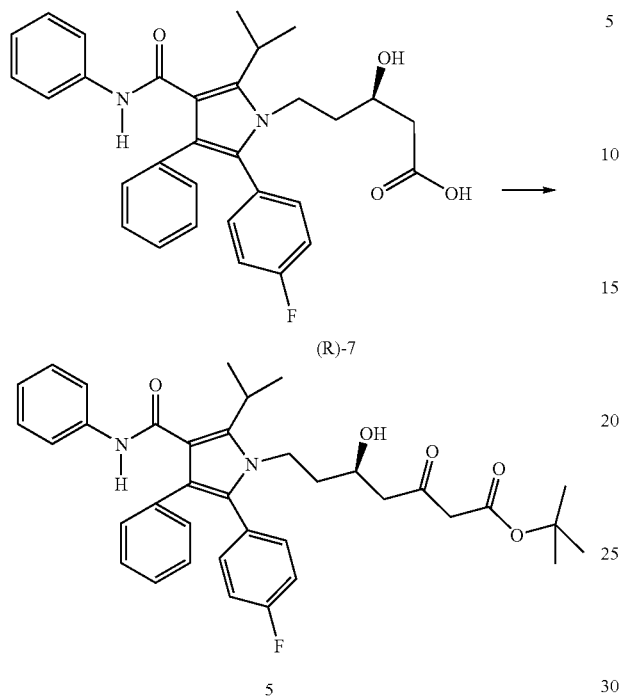

To a suspension of (R)-7 (20 g) in 100 mL methanol at 0-5° C. was added dropwise thionyl chloride (3 mL). The mixture was stirred at room temperature for 1 hour and then the solvent was removed at reduced pressure. The residue was dissolved in ethyl acetate and washed with aqueous saturated $NaHCO_3$, water and brine. After drying and evaporating, the resulting mixture was dissolved in 80 mL anhydrous THF. To the solution was added imidazole (3.0 g) and chlorotrimethylsilane (4.8 mL) at 0-5° C. After stirring at 0-5° C. for 1 hour 60 mL aqueous saturated $NaHCO_3$ was added and the layers were separated and the aqueous phase was extracted with toluene. The combined organic phases were washed with brine and evaporated to about 50 mL. At −35 to −40° C. the solution was added to a lithium enolate of t-butyl acetate prepared by reaction of LDA (60 mL, 2.0 M in heptanes/THF/ethylbenzene) with t-butyl acetate (16 mL). After stirring at −35 to −40° C. for 30-45 min to the reaction mixture was added 80 mL acetic acid and 10 mL water. The resulting mixture was stirred at room temperature for 8 hours followed by adjusting pH to 8 with aqueous NaOH solution. The layers were separated and the aqueous layer was extracted with toluene. The combined organic phases were washed with brine, evaporated to about 50 mL and after adding 50 mL heptanes the mixture was stirred at room temperature for 3 hours. The product 5 was isolated by filtration, washed with toluene/heptanes (1:1) and dried (14.5 g). The analytical data are consistent with the assigned structure.

$^1$H-NMR (300 MHz, $CDCl_3$): δ/ppm=1.45(s, 9H), 1.53 (dd, 6H, $J_1$=1.8 Hz, $J_2$=7.1 Hz), 1.50-1.80(m, 2H), 2.50(s, 1H), 2.53(d, 1H, J=1.9 Hz), 3.30(s, 2H), 3.49-3.61(m, 1H), 3.87-4.00(m, 2H), 4.08-4.20(m, 1H), 6.85(s, 1H), 6.95-7.10 (m, 5H), 7.10-7.22(m, 9H).

Example 5

Preparation of (R)-5-[2-(4-Fluorophenyl)-5-(1-methylethyl)-3-phenyl-4-[(phenylamino)carbonyl]-1H-pyrrol-1-yl]-5-hydroxy-3-oxo-1-heptanoic acid, tert-butylester (5) from the acid (7)

1,1'-Carbonyldiimidazole (0.37 g) was added to a solution of the acid (7) (1.0 g) obtained from Example 2 in 10 mL THF. After stirring at room temperature for 3 hours, the magnesium salt prepared from reaction of magnesium ethoxide (0.58 g) and mono-tert-butyl malonate (1.7 g) was added. The mixture was stirred for 20 hours at room temperature and then the solvent was removed at reduced pressure. The residue was partitioned between ethyl acetate and aqueous 1 M HCl and the layers were separated and the aqueous phase was further extracted with ethyl acetate. The combined organic phases were washed with aqueous saturated $NaHCO_3$ and brine. After drying and purifying, the β-ketoester 5 (0.5 g) was produced. The analytical data are consistent with the assigned structure.

Example 6

Preparation of hydroxy acid 7 in racemic form

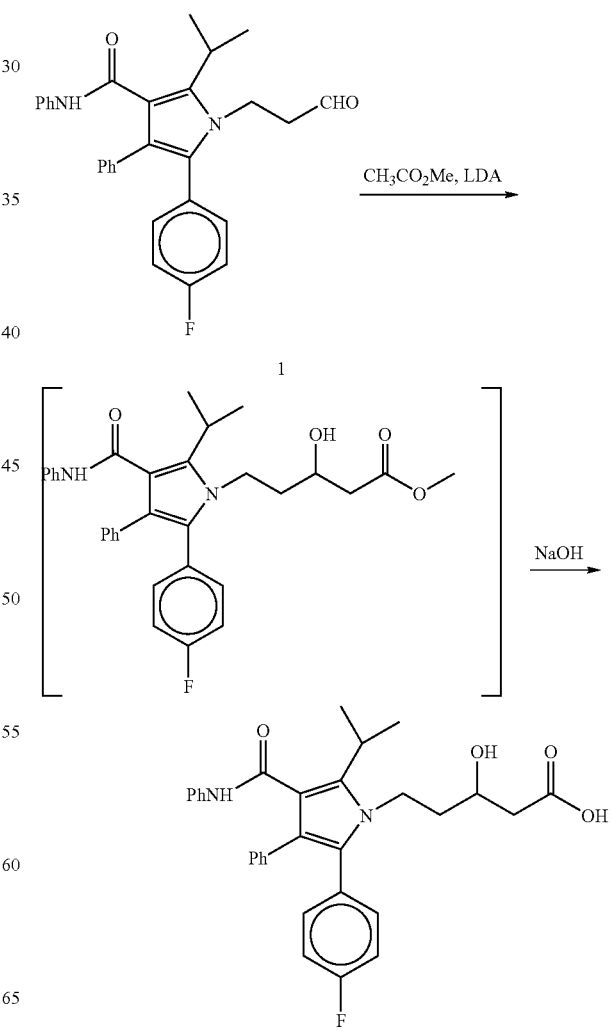

To a solution of 280 mL anhydrous THF and 88 mL 2.0 M LDA in heptanes/THF/ethylbenzene at −78° C. was added dropwise methyl acetate (13 mL). After stirring at −78° C. for 1 h a mixture of 5-(4-fluorophenyl)-2-(1-methylethyl)-1-(3-oxopropyl)-N,4-diphenyl-1H-pyrrole-3-carboxamide (40 g) in 20 mL THF and 88 mL methylene chloride was dropwise added at −78° C. and maintained for 1 h. The mixture was allowed to warm to room temperature after adding 40 mL methanol. Then, 20 mL water and sodium hydroxide (3.5 g) were added followed by reflux for 2 hours. After cooling to room temperature the mixture was adjusted to pH 2-2.5 with 2.0 N HCl solution and the layers were separated and the aqueous phase was extracted with ethyl acetate. The combined organic phases were washed with brine, dried over anhydrous Na$_2$SO$_4$, filtered and evaporated. The residue was treated with 200 mL toluene and the product was filtered, washed with heptanes and dried (38 g). The analytical data are consistent with the assigned structure.

Chiral HPLC: 1:1 R:S-form

Example 7

Resolution of the 1:1 R, S form

To solution of 1:1 R:S-form of 5-[2-(4-fluorophenyl)-5-isopropyl-3-phenyl-4-phenylcarbamoyl-pyrrol-1-yl]-3-hydroxy-pentanoic acid 7 (20 g) in methyl t-butyl ether-methanol (300 ml, 2:1) is added 1 equivalent (R)-methylbenzylamine. The resulting mixture is heated at reflux for 10 hours, cooled to room temperature and filtered. The filter cake is pulped four times in MTBE-MeOH to give 7 g of white powder.

Chiral HPLC: 99:1 (R/S)

Example 8

Preparation of (R)-5-[2-(4-Fluorophenyl)-5-(1-methylethyl)-3-phenyl-4-[(phenylamino)carbonyl]-1H-pyrrol-1-yl]-3-hydroxy-1-pentanoic acid, methylester (3) from (R)-7 methylbenzylamine salt To a suspension of the (R)-7 methylbenzylamine salt (1.1 g) obtained from Example 2 in 5.5 mL methanol with 1 drop of DMF at 0° C. was added dropwise thionyl chloride (0.4 g). The mixture was stirred at room temperature for 2 hours and then the solvent was removed at reduced pressure. The residue was dissolved in ethyl acetate and washed with aqueous saturated NaHCO$_3$, water and brine. After drying and evaporating, the methylester 3 (1.02 g) was produced. The analytical data are consistent with the assigned structure.

Example 9

Preparation of aldehyde 1

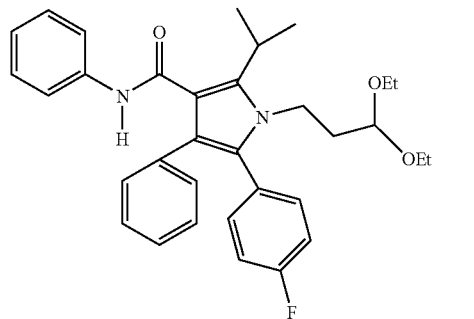

8

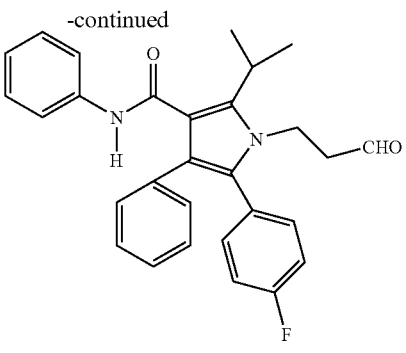

1

Figure 3:
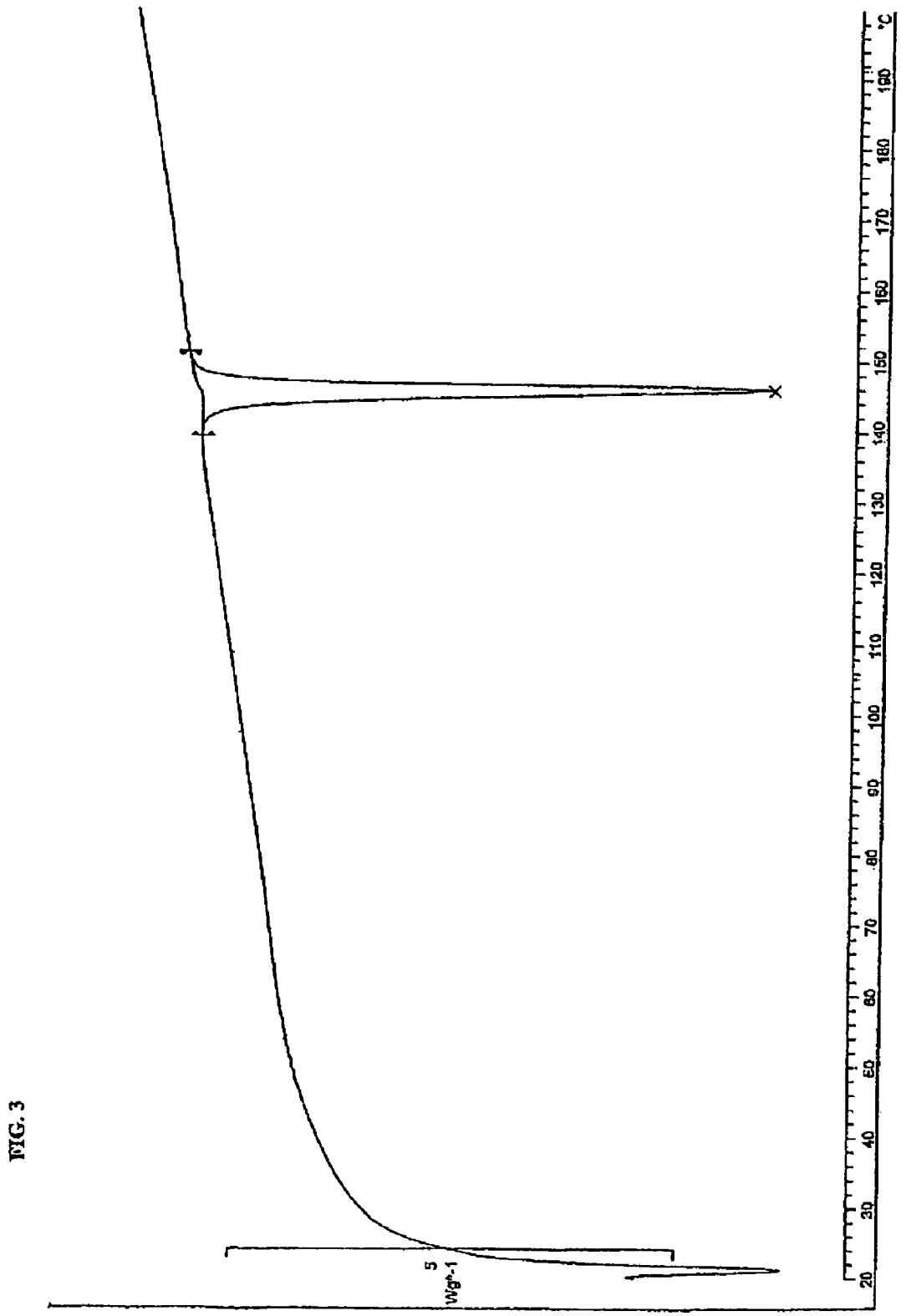
FIG. 3 is the DSC thermogram in the newly discovered Form II polymorph.
Figure 4:
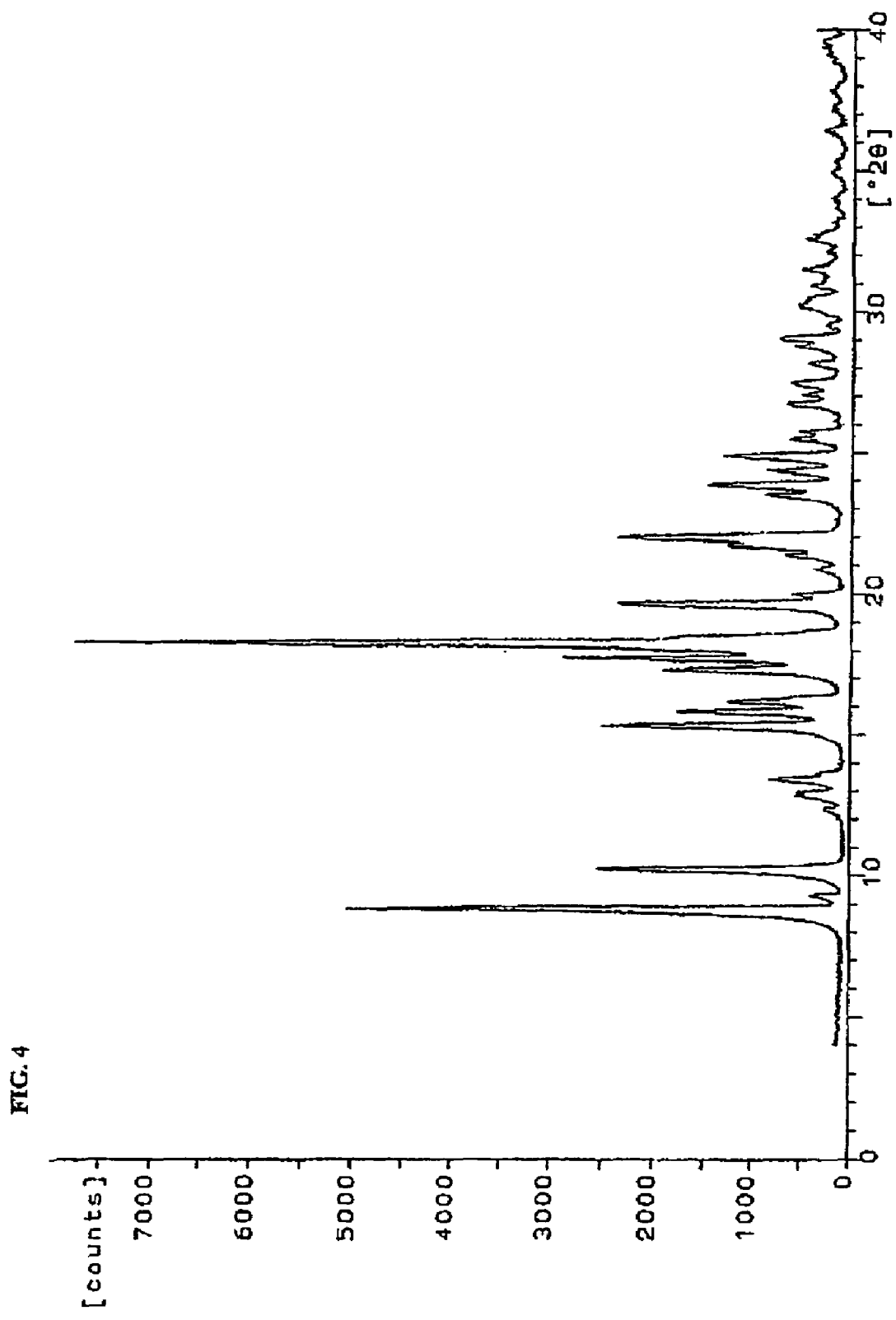
FIG. 4 is the PXRD diffractogram in the newly discovered Form II polymorph.

A suspension of compound 8 (10 g), prepared according to the procedure from U.S. Pat. No. 5,003,080 Example 3, step F when 1-amino-3,3-diethoxypropane was used, in 60 mL acetone and 60 mL 5% HCl solution was stirred at 40° C. for 1 d. The aldehyde 1 was filtered, washed and dried (8 g). The analytical data are consistent with the assigned structure. The DSC thermogram is depicted in FIG. 3 and the PXRD spectrum in FIG. 4.

While the foregoing provides a detailed description of a preferred embodiment of the invention, it is to be understood that this description is illustrative only of the principles of the invention and not limitative. Furthermore, as many changes can be made to the invention without departing from the scope of the invention, it is intended that all material contained herein be interpreted as illustrative of the invention and not in a limiting sense.

What is claimed is:

1. A process for preparing (R)-5-[2-(4-fluorophenyl)-5-(1-methylethyl)-3-phenyl-4-[(phenylamino)carbonyl]-1H-pyrrol-1-yl]-3hydroxyl-1-pentanoic acid 7 comprising:

(a) reacting an aldehyde 1

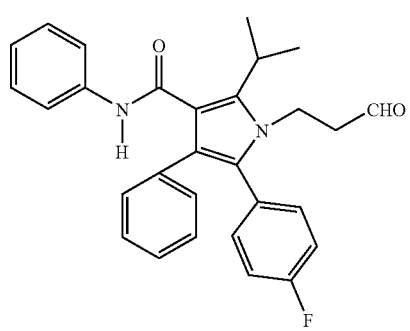

1 with a chiral alkoxy substituted acetate and a chelating co-solvent;

(b) hydrolysis of (R)-5-[2-(4-fluorophenyl)-5-(1-methylethyl)-3-phenyl-4-[(phenylamino)carbonyl]-1H-pyrrol-1-yl]3-hydroxy-1-pentanoic acid, chiral alkoxy ester using a base in a solvent to form a carboxylate 7

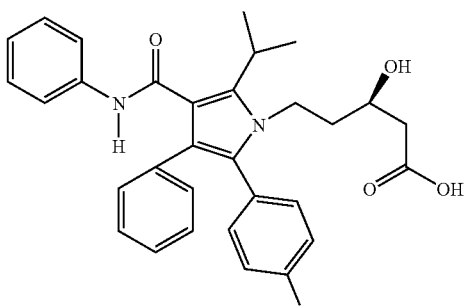

(c) treating the acid with a chiral base to form a salt and purifying the salt.

2. A process for the preparation of (R)-5-[2-(4-fluorophenyl)-5-(1-methylethyl)-3-phenyl-4-[(phenylamino)carbonyl]-1H-pyrrol-1-yl]3hydroxy-1-pentanoic acid 7

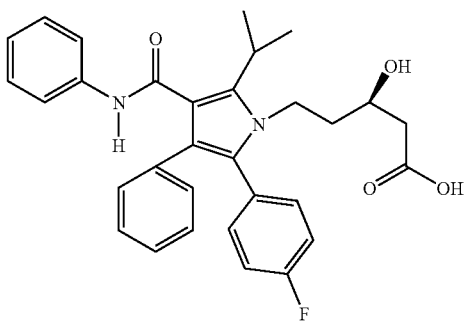

according to claim 1 using S-(−)-2-hydroxy-1,2,2-triphenylethyl acetate as the acetate for step a.

3. A process for the preparation of (R)-5-[2-(4-fluorophenyl)-5-(1-methylethyl)-3-phenyl-4[(phenylamino)carbonyl] 1H-pyrrol-1-yl]-3hydroxy-1-pentanoic acid 7

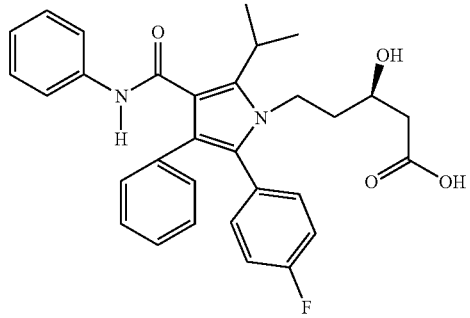

according to claim 1 wherein step a employs a polyether or polyamine as co-solvent.

4. A process for the preparation of (R)-5-[2-(4-fluorophenyl)-5-(1-methylethyl)-3-phenyl-4-[(phenylamino)carbonyl]-1H-pyrrol-1-yl]3-hydroxy-1-pentanoic acid 7

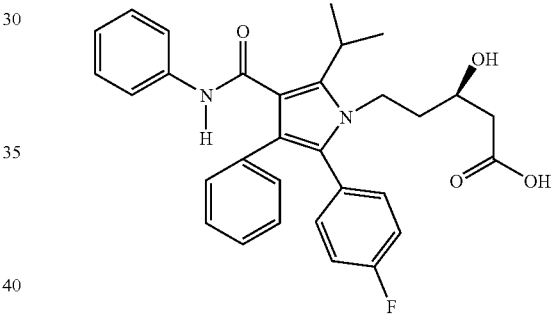

according to claim 1 wherein step a employs diethoxyethane, dimethoxyethane or dioxane as co-solvent.

5. A process for the preparation of (R)-5-[2-(4-fluorophenyl)-5-(1-methylethyl)-3-phenyl-4-[(phenylamino)carbonyl]-1H-pyrrol-1-yl]3-hydroxy-1-pentanoic acid 7

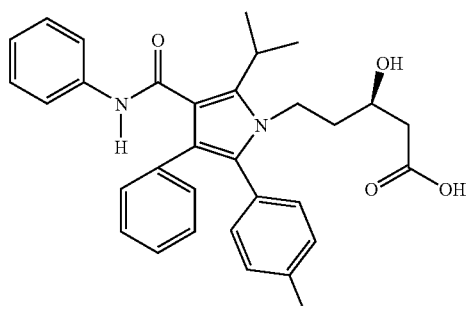

according to claim 1 wherein step a employs N,N,N',N'-tetramethylethylenediamine as co-solvent.

6. A process for the preparation of (R)-5-[2-(4-fluorophenyl)-5-(1-methylethyl)-3-phenyl-4-[(phenylamino)carbonyl]-1H-pyrrol-1-yl]3-hydroxy-1-pentanoic acid 7

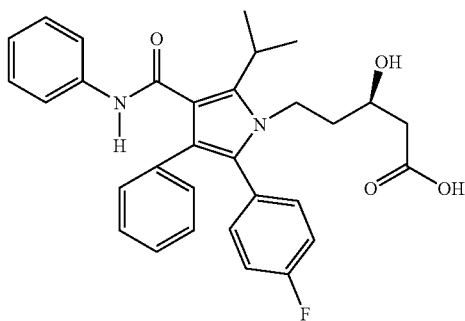

according to claim 1 wherein step b employs lithium hydroxide, sodium hydroxide or potassium hydroxide as a base for the hydrolysis.

7. A process for the preparation of (R)-5-[2-(4-fluorophenyl)-5-(1-methylethyl)-3-phenyl-4-[(phenylamino)carbonyl]-1H-pyrrol-1-yl]3-hydroxy-1-pentanoic acid 7

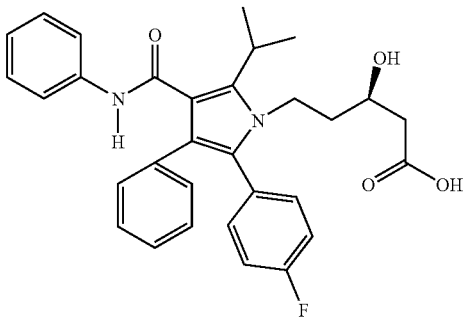

according to claim 1 wherein step c employs (R)- or (S)-methylbenzylamine as resolving agent.

* * * * *